United States Patent
Agnello

(10) Patent No.: US 11,217,344 B2
(45) Date of Patent: Jan. 4, 2022

(54) SYSTEMS AND METHODS FOR CAPTURING DATA FROM A MEDICAL DEVICE

(71) Applicant: Abiomed, Inc., Danvers, MA (US)

(72) Inventor: Alessandro Simone Agnello, Peabody, MA (US)

(73) Assignee: Abiomed, Inc., Danvers, MA (US)

(*) Notice: Subject to any disclaimer, the term of this patent is extended or adjusted under 35 U.S.C. 154(b) by 351 days.

(21) Appl. No.: 15/941,695

(22) Filed: Mar. 30, 2018

(65) Prior Publication Data

US 2018/0374568 A1    Dec. 27, 2018

Related U.S. Application Data

(60) Provisional application No. 62/523,890, filed on Jun. 23, 2017.

(51) Int. Cl.
*G16H 30/20* (2018.01)
*G16H 15/00* (2018.01)
(Continued)

(52) U.S. Cl.
CPC .......... *G16H 30/20* (2018.01); *A61M 60/122* (2021.01); *G06K 9/00523* (2013.01);
(Continued)

(58) Field of Classification Search
CPC ... G06F 1/00–2221/2153; G16H 10/00–80/00; A61B 1/00–2576/026;
(Continued)

(56) References Cited

U.S. PATENT DOCUMENTS 5,832,051 A * 11/1998 Lutz ..................... A61B 6/032
378/8
6,245,019 B1 * 6/2001 Kamiyama ............ A61B 8/481
600/458
(Continued)

FOREIGN PATENT DOCUMENTS

CN          106027664 A       10/2016
EP            1669031 A1 *     6/2006 ............. A61B 5/352
(Continued)

OTHER PUBLICATIONS

Alonazi et al., "Simulation of Motor Current Waveforms in Monitoring Aortic Valve State During Ventricular Assist Device Support," IEEE, 2016, pp. 1451-1454. (Year: 2016).*
(Continued)

*Primary Examiner* — Elaine Gort
*Assistant Examiner* — Jonathon A. Szumny
(74) *Attorney, Agent, or Firm* — Botos Churchill IP Law LLP

(57) ABSTRACT

A method for transferring data from a medical device to a server comprises receiving a video stream from the medical device, capturing an image from the video stream, transmitting the image to the server via a data network, and extracting the data from the image. The image may illustrate and/or represent data over a period of time. The method may also comprise transmitting, from a data module receiving the video stream from the medical device, a signal to a router that indicates that the data module is connected to the network. The method may also comprise transmitting a command to the data module to start capturing the image, transferring the image to the router, broadcasting a signal indicating that the data module has captured the image, receiving the broadcasted signal at the server, and storing the image at the server.

23 Claims, 14 Drawing Sheets

(51) Int. Cl.
  *G16H 30/40*  (2018.01)
  *G16H 40/40*  (2018.01)
  *G06K 9/00*  (2006.01)
  *H04L 29/08*  (2006.01)
  *G06K 9/34*  (2006.01)
  *G06K 9/32*  (2006.01)
  *G16H 40/67*  (2018.01)
  *G16H 10/60*  (2018.01)
  *A61M 60/122*  (2021.01)

(52) U.S. Cl.
  CPC ....... *G06K 9/00979* (2013.01); *G06K 9/3233* (2013.01); *G06K 9/344* (2013.01); *G16H 15/00* (2018.01); *G16H 30/40* (2018.01); *G16H 40/40* (2018.01); *G16H 40/67* (2018.01); *H04L 67/125* (2013.01); *G06K 2209/01* (2013.01); *G16H 10/60* (2018.01)

(58) Field of Classification Search
  CPC .. A61M 1/00–2250/00; G06K 1/00–2215/111; H04L 1/00–2463/146
  See application file for complete search history.

(56) References Cited

U.S. PATENT DOCUMENTS

| | | | | |
|---|---|---|---|---|
| 8,727,992 | B2* | 5/2014 | Takimoto | A61B 8/06 600/441 |
| 9,931,090 | B2* | 4/2018 | Sakaguchi | A61B 6/12 |
| 10,143,435 | B2* | 12/2018 | Hosoki | G16H 50/30 |
| 2002/0091331 | A1* | 7/2002 | Onoda | A61B 5/04325 600/509 |
| 2005/0111762 | A1* | 5/2005 | Mathew | G06T 5/005 382/309 |
| 2005/0135306 | A1* | 6/2005 | McAllen | H04L 29/06 370/329 |
| 2007/0223574 | A1* | 9/2007 | Roman | H04N 19/90 375/240.01 |
| 2008/0114240 | A1* | 5/2008 | Sasaki | A61B 8/06 600/440 |
| 2008/0123915 | A1* | 5/2008 | Nagy | G16H 30/40 382/128 |
| 2010/0080206 | A1* | 4/2010 | Yamada | H04W 48/14 370/338 |
| 2010/0228508 | A1* | 9/2010 | Smith | G01R 13/02 702/68 |
| 2011/0137169 | A1* | 6/2011 | Akaki | A61B 8/463 600/443 |
| 2011/0224550 | A1* | 9/2011 | Shinohara | G01S 15/8993 600/443 |
| 2012/0020563 | A1* | 1/2012 | Amir | G06K 9/346 382/182 |
| 2012/0071828 | A1* | 3/2012 | Tojo | A61M 5/20 604/131 |
| 2012/0218404 | A1* | 8/2012 | Buxton | H04N 7/183 348/121 |
| 2012/0253848 | A1* | 10/2012 | Gazula | G06F 19/00 705/3 |
| 2012/0330557 | A1* | 12/2012 | Zhang | A61B 6/5217 702/19 |
| 2012/0330680 | A1 | 12/2012 | O'Larte | |
| 2013/0033978 | A1* | 2/2013 | Eckert | H04L 45/28 370/216 |
| 2013/0158349 | A1* | 6/2013 | Ashida | A61B 1/0016 600/109 |
| 2013/0273968 | A1* | 10/2013 | Rhoads | H04W 4/50 455/556.1 |
| 2013/0308839 | A1* | 11/2013 | Taylor | G06T 7/0012 382/128 |
| 2014/0079297 | A1 | 3/2014 | Tadayon et al. | |
| 2014/0270536 | A1 | 9/2014 | Amtrup et al. | |
| 2014/0280882 | A1* | 9/2014 | LaCerte | G06F 19/3418 709/224 |
| 2014/0351738 | A1* | 11/2014 | Kokovidis | A61B 5/7445 715/771 |
| 2015/0016700 | A1* | 1/2015 | Drozdzal | G06T 11/60 382/128 |
| 2015/0038771 | A1* | 2/2015 | Marseille | A61M 1/1086 600/16 |
| 2015/0082039 | A1* | 3/2015 | Stalzer | H04L 63/0853 713/171 |
| 2015/0302605 | A1* | 10/2015 | Sasaki | A61B 6/467 382/128 |
| 2015/0367136 | A1* | 12/2015 | Rondoni | A61N 1/37217 607/42 |
| 2016/0120491 | A1* | 5/2016 | Shimamura | G06T 7/0016 348/333.05 |
| 2016/0189400 | A1* | 6/2016 | Li | G06K 9/46 382/131 |
| 2017/0082717 | A1* | 3/2017 | London | G01N 33/4833 |
| 2017/0105662 | A1* | 4/2017 | Silawan | A61B 5/021 |
| 2017/0148158 | A1* | 5/2017 | Najarian | A61B 5/7203 |
| 2017/0231508 | A1* | 8/2017 | Edwards | A61B 8/565 600/301 |
| 2017/0264442 | A1* | 9/2017 | Namiki | H04L 9/0643 |
| 2017/0266379 | A1* | 9/2017 | Harrity | A61M 5/1723 |
| 2017/0340789 | A1* | 11/2017 | Bonde | A61M 1/101 |
| 2017/0351708 | A1* | 12/2017 | Lahmann | G06K 9/6892 |
| 2018/0025704 | A1* | 1/2018 | Gopishankar | G06T 11/001 345/629 |
| 2018/0168473 | A1* | 6/2018 | Du | A61B 5/6833 |
| 2018/0204326 | A1* | 7/2018 | Noji | G06T 7/248 |
| 2018/0286500 | A1* | 10/2018 | Sole Guerra | G16H 10/60 |
| 2019/0020644 | A1* | 1/2019 | Asai | H04L 67/146 |

FOREIGN PATENT DOCUMENTS

| | | |
|---|---|---|
| EP | 2980694 A2 | 2/2016 |
| JP | 2014-241089 A | 12/2014 |
| WO | 2006/020862 A2 | 2/2006 |
| WO | 2007/038254 A2 | 4/2007 |

OTHER PUBLICATIONS

ISR dated Oct. 31, 2018 PCT/US2018/038933 (2 pages).

* cited by examiner

SYSTEMS AND METHODS FOR CAPTURING DATA FROM A MEDICAL DEVICE

CROSS-REFERENCE TO RELATED APPLICATION

This application claims the benefit of U.S. Provisional Application No. 62/523,890, filed on Jun. 23, 2017, the content of which is hereby incorporated herein by reference in its entirety.

FIELD OF THE INVENTION

The present disclosure relates to systems and methods for implementing a cloud based architecture with a portal that controls destinations of video streaming, data upload, and notifications from medical devices to client devices using optical character recognition and digital signal processing with scalability to an indefinite amount of users.

BACKGROUND

Medical devices monitoring a patient generate a large amount of data since they operate continuously. Many of these medical devices have a graphical display to deliver the data they are monitoring but medical professionals need to be physically near the medical device to observe the data from the graphical display. In addition, the information on the graphical display often includes waveforms and other data represented by plots.

However, there remains a long felt need to remotely access these medical devices in order to allow medical professionals to monitor a patient without having to be physically present. In addition, there is a need to implement a system to capture information from the graphical display in order to extract information from the waveforms and plots displayed and deliver the information to medical professionals remotely.

SUMMARY OF INVENTION

The present disclosure relates to a method for transferring data from a medical device to a server. The method comprises receiving data video stream from the medical device. Further, the method comprises capturing a first image from the video stream at a first time. The first image may represent and/or illustrate first medical data over a first period of time. The method further comprises transmitting the first image to the server via a data network. The method also comprises extracting, at the server, the first medical data from the first image.

According to one implementation, the method further comprises capturing a second image from the video stream at a second time. The second image may represent and/or illustrate second medical data over a second period of time. The method further comprises transmitting the second image to the server via a data network. The method also comprises extracting, at the server, the second medical data from the second image.

In some implementations, the second period of time starts after the first period of time. In other implementations, the first period of time and the second period of time have the same duration. In certain implementations, the duration is equal to or greater than about one of 1 second, 2 seconds, 3 seconds, 4 seconds, 5 seconds, 10 seconds, 20 seconds, 30 seconds, and 1 minute. According to some implementations, the first period of time and the second period of time have different durations.

In some implementations, extracting the first and second medical data from the first and second images includes optical character recognition (OCR) of the first and second images.

According to some implementations, the method further comprises sensing via at least one of a pressure sensor, temperature sensor, flow rate sensor, voltage sensor, current sensor, optical sensor, and audio sensor. In some implementations, the first and second medical data includes pressure, flow rate, pump speed, temperature, voltage, current, and biometric conditions.

In other implementations, the method further comprises repeatedly performing the features of claim 1 and claims 2. According to some implementations, the server is a web server. In some implementations, the medical device is an intravascular blood pump.

In certain implementations, the method further comprises transmitting, from a data module receiving the video stream from the medical device, a first signal to a router that indicates that the data module is connected to the network. Further, the method comprises transmitting, from the router, a command to the data module to start capturing the first image. The method further comprises transferring the first image to the router from the data module. The method also comprises broadcasting, from the router, a second signal indicating that the data module has captured the first image. Further, the method comprises receiving, at the server, the broadcasted second signal from the router. The method further comprises storing the first image at the web server.

According to some implementations, the method further comprises connecting the data module to the data network.

A second aspect of the present disclosure relates to a system comprising a data module, a router, a client device, and a server. The data module may be configured to receive data from a medical device. The router may be communicatively coupled to the data module, and may be configured to receive the data from the data module and store the data in storage. The client device may be configured to display the data. The server may be communicatively coupled to the client device and the router, and may be configured to receive a request to access the data from the client device, receive the data from storage, and transmit the data to the client device.

A third aspect of the present disclosure relates to a method for extracting data from an image. The method comprises receiving a first image. The first image may represent and/or illustrate data from a medical device. Further, the method comprises masking first portions of the first image. The first image may comprise the first portions and second portions of the first image. The method further comprises generating a second image consisting of the second portions of the first image. The method also comprises extracting, using optical image recognition, data from the second image.

According to one implementation, the first image is captured from a video stream from the medical device.

In some implementations, the method further comprises extracting, using optical character recognition, first data from a first portion of the second image. Further, the method comprises determining a validity of the first data by comparing the first data to reference data. The method also comprises, in response to determining that the first data is valid, extracting, using optical character recognition, second data from a second portion of the second image.

According to some implementations, the method further comprises, in response to determining that the first data is not valid, broadcasting a signal indicating that the first data is not valid. Further, the method comprises receiving a third image. The third image may represent and/or illustrate data from the medical device.

In certain implementations, masking the first portions of the first image comprises selecting an image mask based on the size of the first image and occluding the first portions of the first image using the image mask.

In some implementations, the method further comprises extracting, using digital signal processing, waveform data from a waveform in the second image.

According to some implementations, the method further comprises selecting a first pixel from the second image. The first pixel may represent and/or illustrate a color. Further, the method comprises determining the color of the first pixel. The color of the first pixel may correspond to an alarm severity. The method also comprises determining the alarm severity based on the color of the first pixel. In certain implementations, the method further comprises selecting a second pixel from the second image and determining the alarm severity based on the first pixel and the second pixel.

BRIEF DESCRIPTION OF THE DRAWINGS

The foregoing and other objects and advantages will be apparent upon consideration of the following detailed description, taken in conjunction with the accompanying drawings, in which like reference characters refer to like parts throughout, and in which.

DETAILED DESCRIPTION

Figure 1:
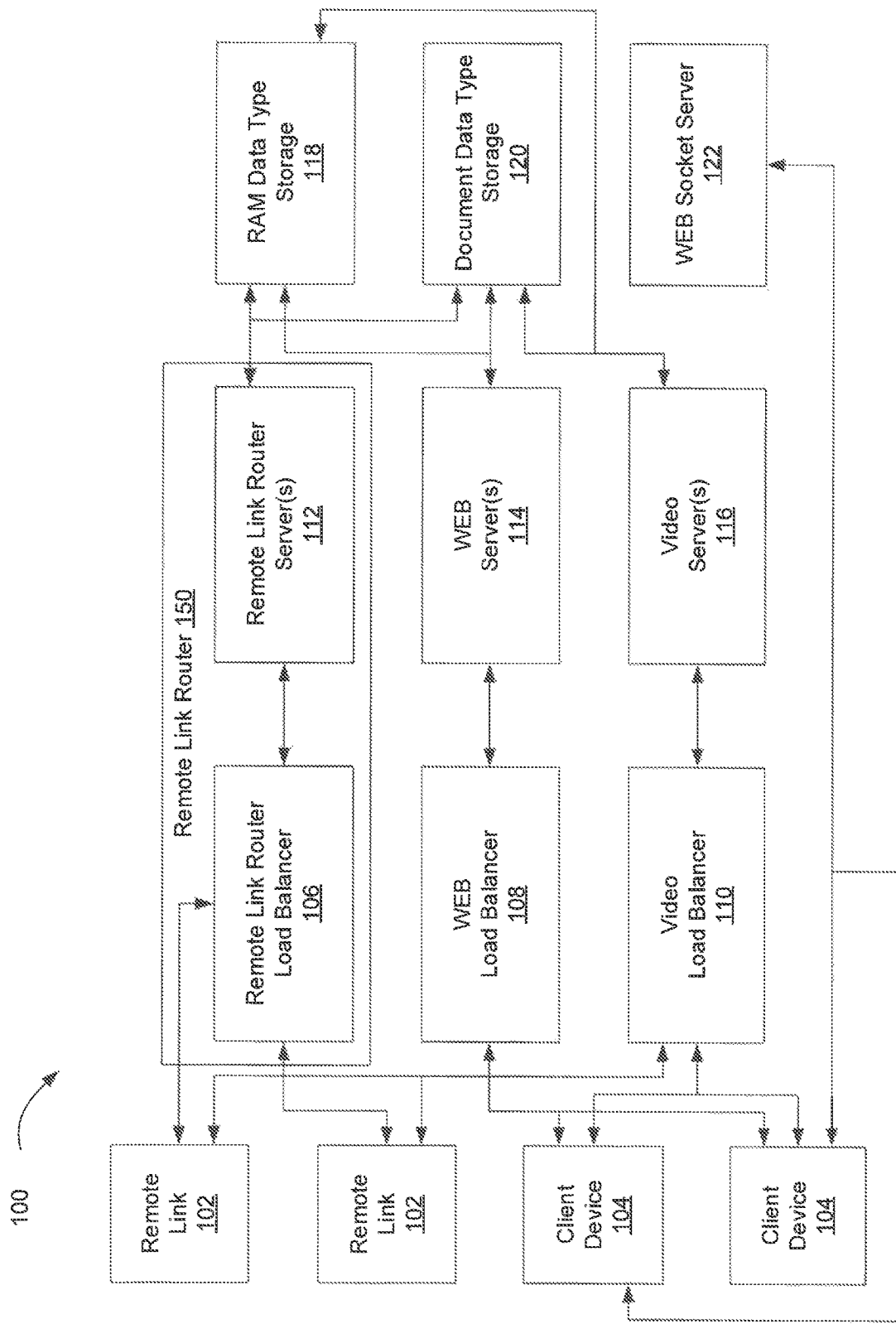
FIG. 1 shows a schematic representation of a remote link architecture, configured according to one or more aspects of the present disclosure.

FIG. 1 is a schematic representation of a remote link architecture 100. Remote link architecture 100 includes remote link 102, client device 104, remote link router (RLR) 150, WEB load balancer 108, video load balancer 110, WEB server 114, video server 116, random-access memory (RAM) data type storage 118, document data type storage 120, and WEB socket server 122.

Remote link 102 may be embedded in a medical device that is monitoring a patient at a hospital, clinic, the patient's house, or another location. Remote link 102 captures images and deliver video streams from the medical device display and transmit the images and video to the remote link router 150. Remote link architecture 100 may comprise multiple remote links 102. Remote link 102 interacts with the rest of remote link architecture 100 through RLR 150. RLR 150 includes an RLR load balancer 106 and RLR server 112. RLR 150 may comprise multiple RLR servers 112. RLR server 112 may include a custom protocol used to communicate with one or more remote links 102. RLR load balancer 106 manages the load to one or more RLR servers 112. RLR load balancer 106 may generate a priority for multiple remote links 102. The priority may be based on preferences obtained from the client device 104. In other aspects, the priority is based on preferences obtained from the remote links 102. In another aspect, the priority is based on preferences obtained from the RLR server 112.

Client device 104 may be a personal computer, a tablet, or a mobile device with an internet connection. A medical professional using client device 104 may be interested in obtaining information from one or multiple remote links 102. Images captured by a remote link 102 may be accessed by the client device 104. In addition, if the medical professional is interested in observing a live video stream of the medical device embedded with remote link 102, the client device can display the video stream. Remote link architecture may comprise multiple client devices 104. A single client device 104 may access multiple remote links 102, as long as the client device has access to the remote links 102.

WEB load balancer 108 controls the load to one or more WEB servers 114. WEB server 114 may include a mechanism for clients to view information, data, and video streams from one or more remote links 102. WEB load balancer 108 may generate a priority for multiple client devices 104. The priority may be based on preferences obtained from the client devices 104. In other aspects, the priority is based on preferences obtained from the remote links 102. In another aspect, the priority is based on preferences obtained from the WEB server 114. WEB socket server 122 may push messages to groups of client devices 104. Upon client device 104 connection to the WEB server 114, the client device 104 will register to the WEB socket server 122 for messages for either one or multiple remote links 102. The WEB socket server 122 will receive messages that will be applicable to one or more remote links 102. This message with associated data will be broadcasted to all connected client devices 104 for updates from those remote links 102.

Video load balancer 110 controls the load to one or more video servers 116. Video server 116 may be the receiver and sender of video streams from one or more remote links 102. Video load balancer 110 may generate a priority for multiple client devices 104. The priority may be based on preferences obtained from the client devices 104. In other aspects, the priority is based on preferences obtained from the remote links 102. In another aspect, the priority is based on preferences obtained from the video server 116.

RAM data type storage 118 may be volatile storage that can be accessed quickly. RAM data type storage 118 may comprise dynamic random-access memory (DRAM), static random-access memory (SRAM), or another type of high-speed volatile memory. Images captured by remote link 102 may be stored in RAM data type storage 118 before being transmitted to client device 104. RAM data type storage 118 may also store video streams captured by remote link 102. Document data type storage 120 may be non-volatile storage that can maintain data for long periods of time. Document data type storage 120 may be hard disks, optical disks, solid-state drives (SSDs), or another type of non-volatile memory.

Figure 2:
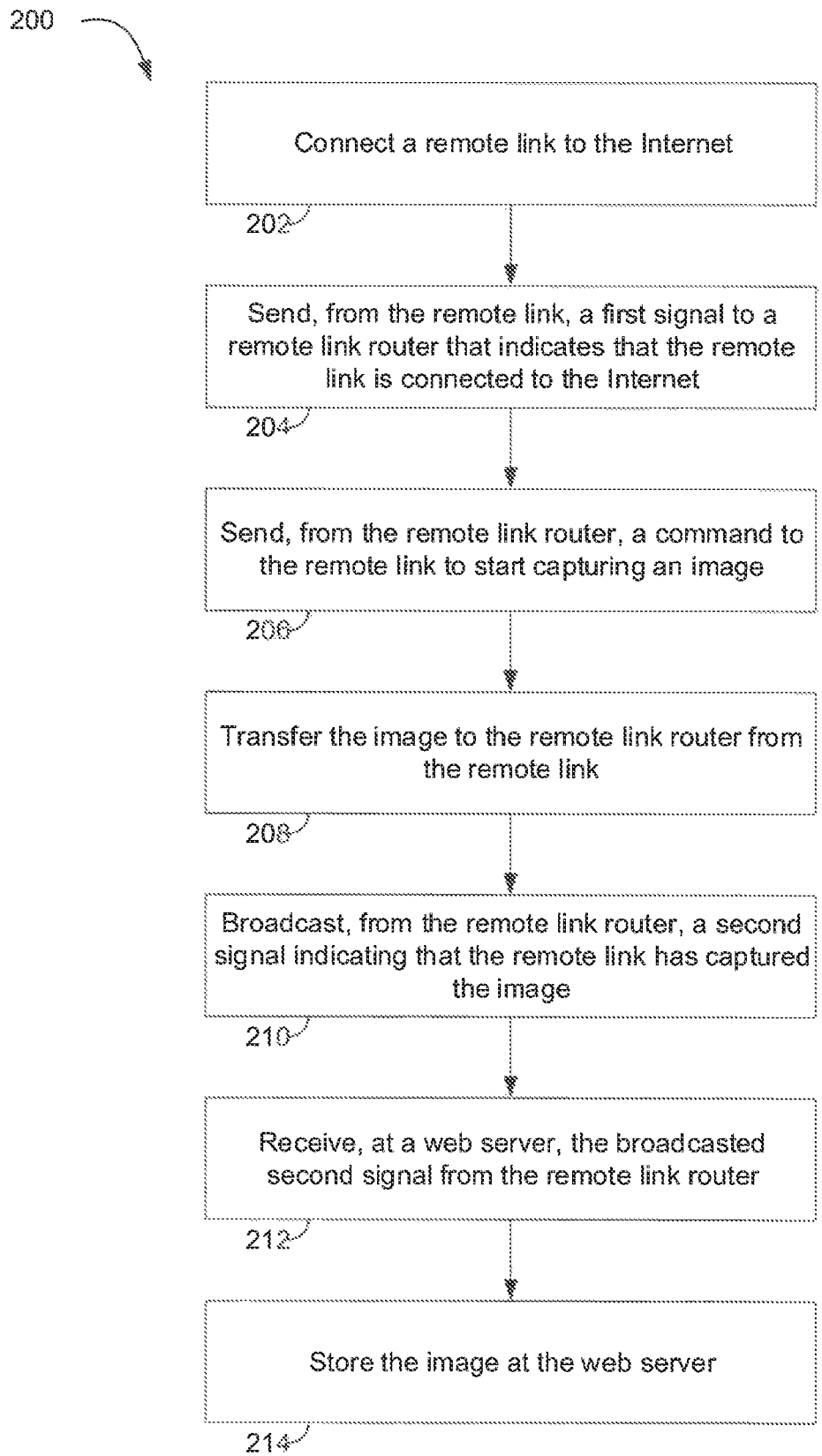
FIG. 2 is a flow diagram of method steps for transferring data from a medical device to a server, according to an aspect of the present disclosure.

A process 200 of transferring an image from a remote link 102 to a remote link router server 112 is illustrated in FIG. 2. Process 200 begins by connecting a remote link 102 to the internet at step 202. Step 202 may include a process to initialize remote link 102 as described below by process 500 in FIG. 5.

Process 200 continues by sending, from the remote link 102, a first signal to an RLR 150 that indicates that the remote link 102 is connected to the internet as step 204. The first signal may be sent directly to the RLR load balancer 106. In another aspect, the first signal may be sent directly to the RLR server 112.

Process 200 continues by sending, from the RLR 150, a command to the remote link 102 to start capturing an image at step 206. For example, remote link 102 uses image capture unit 626, described below, to capture the image from a medical device.

Process 200 continues by transferring the image to the RLR 150 from the remote link 102 at step 208. For example, RLR load balancer manages the transfer of the image from the remote link 102 to the RLR server 112. Once the image has been transferred to the RLR server 112, process 200 continues to step 210.

Process 200 continues by broadcasting, from the RLR 150, a second signal indicating that the remote link 102 has captured the image at step 210. For example, RLR 150 broadcasts the second signal such that the WEB servers 114 are notified that RLR 150 has the image captured by remote link 102.

Process 200 continues by receiving, at a WEB server 114, the broadcasted second signal from the remote link 102 at step 212. For example, WEB server 114 receives the broadcasted signal from RLR 150 so that the WEB server 114 is notified that RLR 150 has the image captured by remote link 102.

Process 200 finishes by storing the image at the WEB server 114 at step 214. The image may be stored in RAM data type storage 118. For example, RLR 150 transfers the image to WEB server 114, after which WEB server 114 transfers the image to RAM data type storage 118. In one aspect, RLR 150 may transfer the image directly to RAM data type storage 118.

Figure 3:
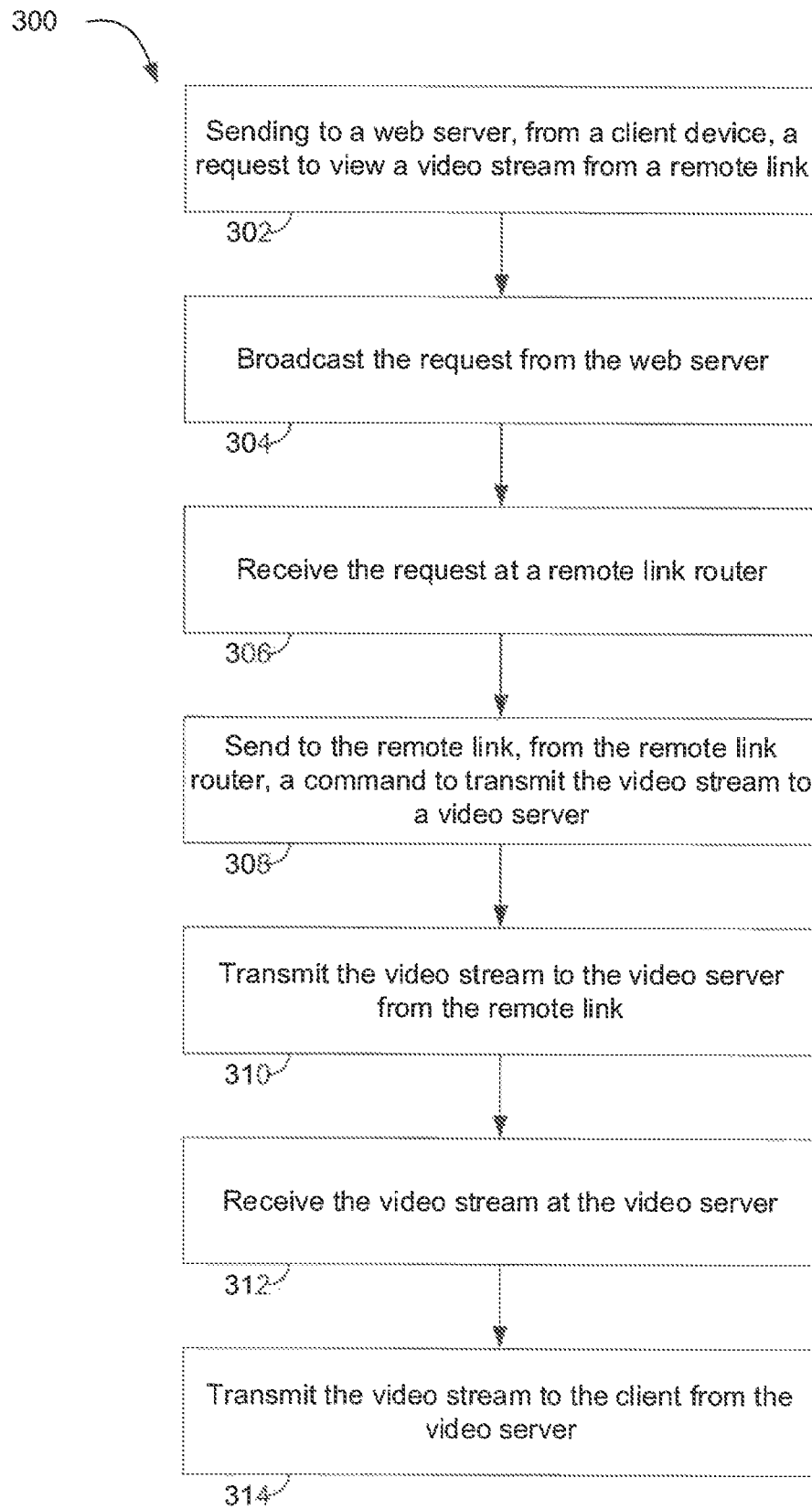
FIG. 3 is a flow diagram of method steps for transferring data from a medical device to a server, according to an aspect of the present disclosure.

A process 300 of transferring a video stream from a remote link 102 to a client device 104 is illustrated in FIG. 3. Process 300 begins by sending to a WEB server 114, from a client device 104, a request to view a video stream from a remote link 102 at step 302. The request may be sent through WEB load balancer 108 before being transmitted to the WEB server 114. In one aspect, the request may include information identifying the remote link 102 that is to be accessed.

Process 300 continues by broadcasting the request from the WEB server 114 at step 304. For example, the WEB server 114 notifies the RLRs 150 that a client device 104 has requested to view a video stream from a remote link 102 by broadcasting the request to all of the RLRs 150.

Process 300 continues by receiving the request at an RLR 150 at step 306. For example, RLR server 112 receives the request from the WEB server 114. In one aspect, RLR 150 receives the request after determining that the request identifies a remote link 102 that is communicatively coupled to the RLR 150.

Process 300 continues by sending to the remote link 102, from the RLR 150, a command to transmit the video stream to a video server 116 at step 308. For example, RLR server 112 transmits a signal through RLR load balancer 106 to remote link 102 that initiates a process to transmit a video stream from the remote link 102 to the video server 116.

Process 300 continues by transmitting the video stream to the video server 116 from the remote link 102 at step 310. In one aspect, the remote link 102 transmits the video stream to the video load balancer 110 which determines which video server 116 to send the video stream. The video load balancer 110 may make the determination based on the load of the video servers 116 and a priority of the remote link 102 and client device 104.

Process 300 continues by receiving the video stream at the video server 116 at step 312. For example, once video load balancer 110 determines which video server 116 can receive the video stream, the video server 116 receives the video stream.

Process 300 finishes by transmitting the video stream to the client device 104 from the video server 116. For example, the video server 116 initiates transfer of the video stream to the client device 104 through video load balancer 110.

Figure 4:
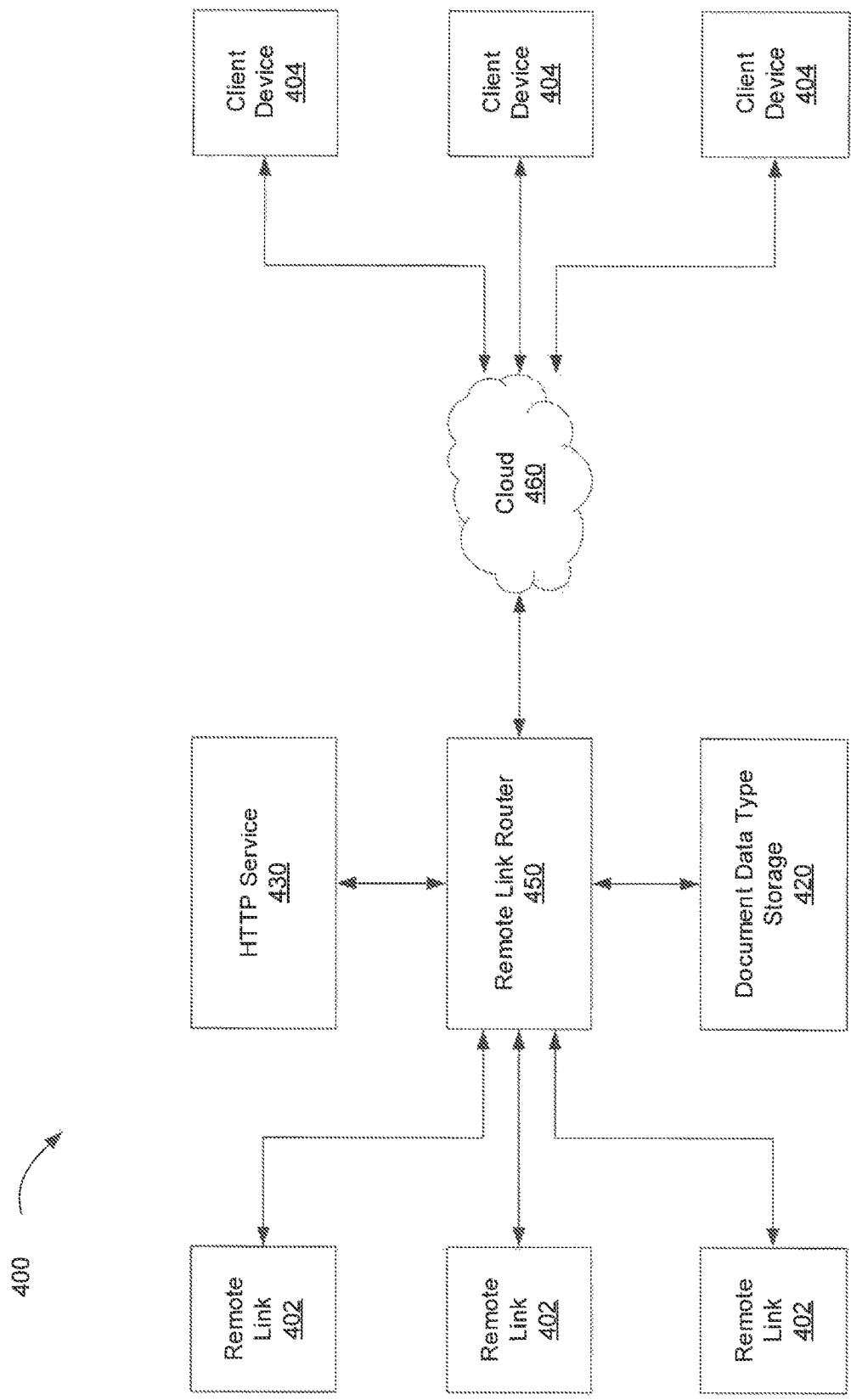
FIG. 4 shows a schematic representation of a remote link architecture, configured according to one or more aspects of the present disclosure.

FIG. 4 shows a schematic representation of a remote link architecture 400. Remote link architecture 400 includes remote link 402, client device 404, RLR 450, document data type storage 420, HTTP service 430, and cloud 460.

Remote link 402 is similar to remote link 102 and may be embedded in a medical device that is monitoring a patient at a hospital, clinic, the patient's house, or another location. Remote link 402 may capture images and deliver video streams from the medical device display and transmit the images and video to the remote link router 450. Remote link architecture 400 may comprise multiple remote links 402. Remote link 402 interacts with the rest of remote link architecture 400 through RLR 450. RLR 450 is similar to RLR 150 described above.

Client device 404 is similar to client device 104 and may be a personal computer, a tablet, or a mobile device with an internet connection. A medical professional using client device 404 may be interested in obtaining information from one or multiple remote links 402. Images captured by a remote link 402 may be accessed by the client device 404. In addition, if the medical professional is interested in observing a live video stream of the medical device embedded with remote link 402, the client device can display the video stream. Remote link architecture may comprise multiple client devices 404. A single client device 404 may access multiple remote links 402, as long as the client device has access to the remote links 402. Client device 404 may communicate with RLR 450 through cloud 460. Cloud 460 represents a network of internet-based devices and connections such as servers, storage, and applications.

Document data type storage 420 is similar to document data type storage 120 and may be non-volatile storage that can maintain data for long periods of time. Document data type storage 420 may be hard disks, optical disks, solid-state drives (SSDs), or another type of non-volatile memory. Document data type storage 420 may store Wi-Fi credentials or other initialization information obtained from one or more client devices 404 or from RLR 450. Document data type storage 420 may transmit the Wi-Fi credentials or other initialization information to RLR 450 or directly to one or more remote links 402.

HTTP service 430 may be a framework that provides the ability for the RLR 450 to make HTTP requests. RLR 450 may use HTTP service 430 to obtain Wi-Fi credentials or other initialization information and store the information in document data type storage 420.

Figure 5:
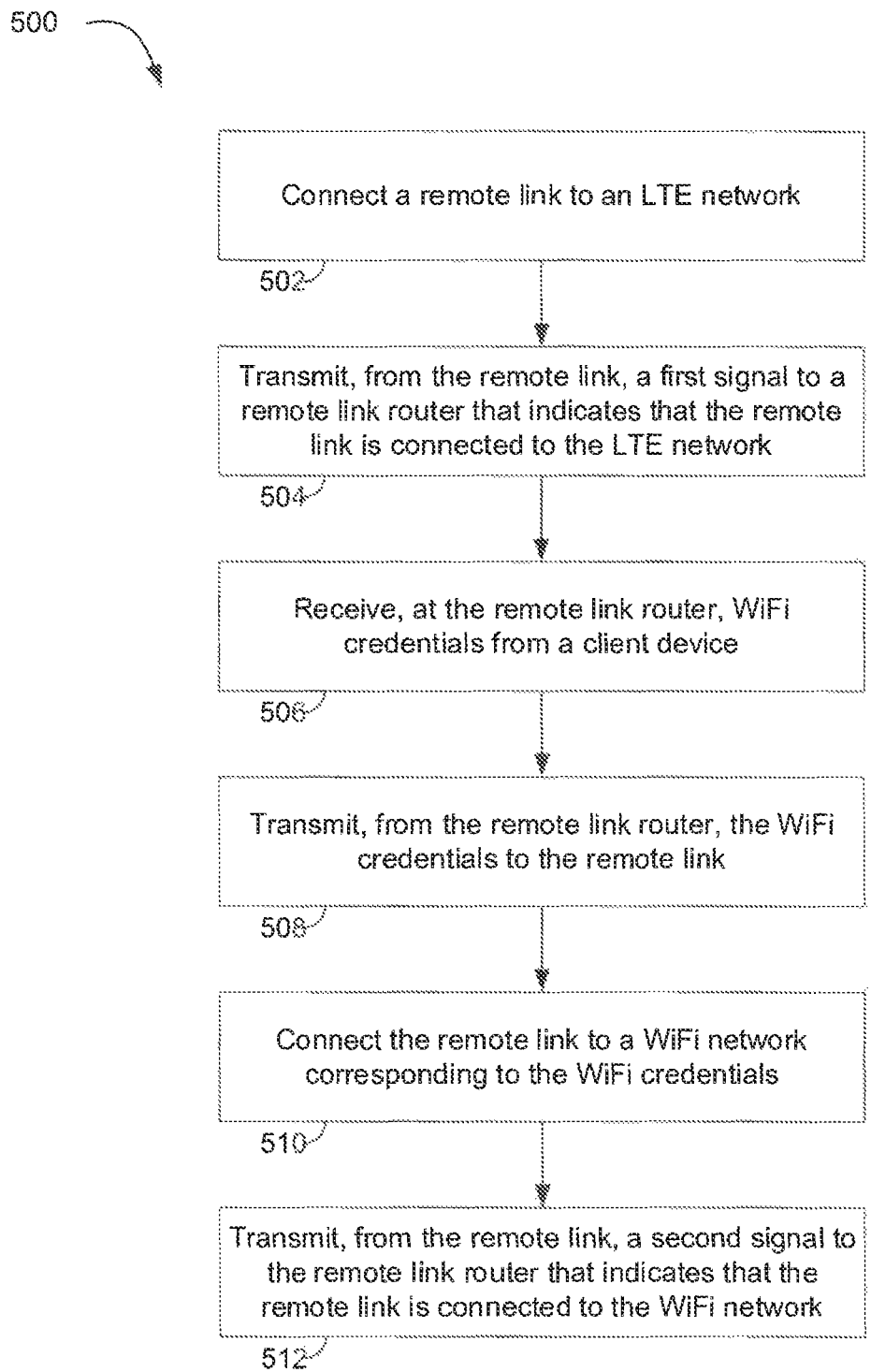
FIG. 5 is a flow diagram of method steps for initializing a remote link, according to an aspect of the present disclosure.

A process 500 of initializing a remote link 402 is illustrated in FIG. 5. Process 500 begins by connecting a remote link 402 to an LTE network at step 502. In another aspect, the remote link 402 may connect to a 3G or 4G network.

Process 500 continues by transmitting, from the remote link 402, a first signal to an RLR 450 that indicates that the remote link 402 is connected to the LTE network at step 504. For example, once the remote link 402 is online, it transmits a signal to the RLR 450 in order to notify the RLR 450 that it is ready to transmit or receive data. In one aspect, the RLR 450 is also connected to the LTE network.

Process 500 continues by receiving, at the RLR 450, Wi-Fi credentials from a client device 404 at step 506. For example, a user inputs the Wi-Fi credentials onto a client device 404 which then transmits the Wi-Fi credentials to the RLR 450. In one aspect, RLR 450 has the Wi-Fi credentials stored.

Process 500 continues by transmitting, from the RLR 450, the Wi-Fi credentials to the remote link 402 at step 508. For example, the RLR 450 transmits the Wi-Fi credentials to the remote link 402 using the LTE network.

Process 500 continues by connecting the remote link 402 to a Wi-Fi network corresponding to the Wi-Fi credentials at step 510. For example, once the remote link 402 has received the Wi-Fi credentials, remote link 402 searches for the Wi-Fi network identified by the Wi-Fi credentials and connect to it.

Process 500 finishes by transmitting, from the remote link 402, a second signal to the RLR 450 that indicates that the remote link 402 is connected to the Wi-Fi network. For example, in order to confirm that the remote link 402 has successfully connected to the Wi-Fi network, remote link 402 sends a signal to the RLR 450 using the Wi-Fi network that indicates that it has successfully connected. In another aspect, remote link 402 sends the signal to the RLR 450 using the LTE network if the connection is faster than the Wi-Fi network. In one aspect, if the remote link 402 cannot connect to the Wi-Fi network, it sends a signal to the RLR 450 using the LTE network that indicates that the connection was not successful.

Figure 6:
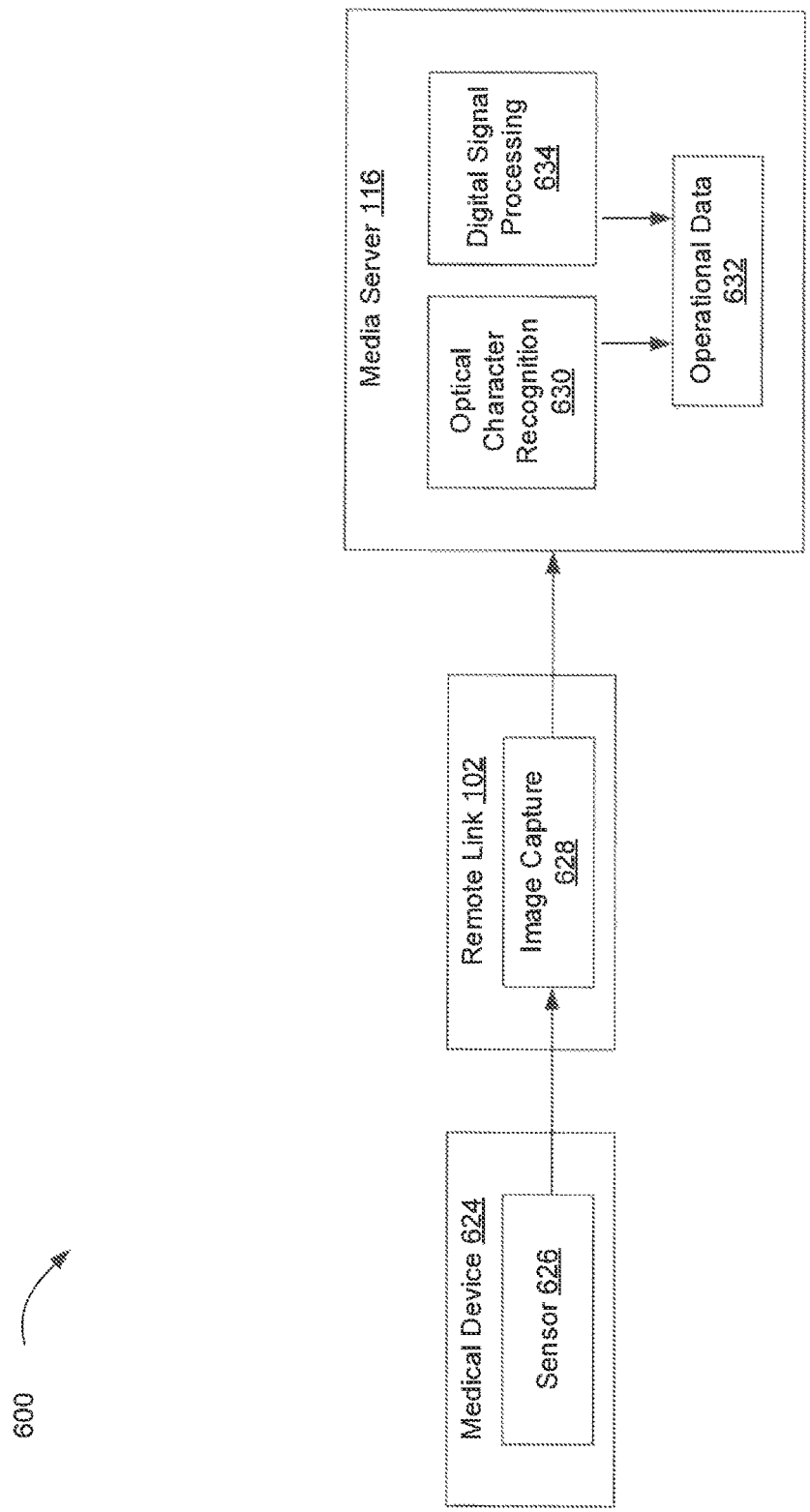
FIG. 6 shows a schematic representation of a remote link architecture, configured according to one or more aspects of the present disclosure.

FIG. 6 shows a schematic representation of a remote link architecture 600. Remote link architecture 600 includes medical device 624, remote link 102, and media server 116. Medical device 624 may include a sensor 626. Remote link 102 may include an image capture unit 628. Media server 116 may include an optical character recognition unit 630 and operational data unit 632.

Medical device 624 may be a medical device that is monitoring a patient at a hospital, clinic, the patient's house, or another location. Medical device 624 includes a sensor 626 that may be measuring and recording health signals from a patient. The sensor 626 may be a pressure sensor, temperature sensor, flow rate sensor, voltage sensor, current sensor, optical sensor, or audio sensor.

Image capture unit 628 may be an application that enables remote link 102 to capture images from sensor 626. For example, image capture unit 628 captures an image of the display of medical device 624. The image of the display of medical device 624 may include data from sensor 626 represented alphanumerically or graphically, in a waveform plot. Image capture unit 628 may convert analog data captured from sensor 626 into digital data that may be used by optical character recognition unit 630. For example, image capture unit 628 converts an analog signal from a video graphics array (VGA) connection from sensor 626. Optical character recognition (OCR) may be used to convert images of text or shapes into digital data, as further described in relation to FIGS. 10-14. In another aspect, other OCR equivalents, and/or digital signal processing (DSP) may be used to extract data from images.

OCR unit 630 may be an application that electronically converts images of text or shapes into digital data. For example, OCR unit 630 analyzes the image captured by image capture unit 628 in remote link 102 to extract data from the data embedded in the image. The OCR unit 630 may be able to extract data from a waveform.

In one aspect, media server 116 may include a DSP unit 634. DSP unit 634 may be an application that converts images into digital data. For example, DSP unit 634 converts the image captured by image capture unit 628 in remote link 102 to digital data. Once in digital form, media server 116 may identify and/or filter the operational and/or medical data that is embedded in the image. In another aspect, DSP unit 634 may be used to extract data from a waveform included in the image. For example, OCR unit 630 extracts a period from a waveform portion of an image and DSP unit 634 uses the period and boundaries of the waveform to extract operational and/or medical data. By using the period and boundaries of the waveform portion of the image, DSP unit 634 associates the pixels in the waveform portion with a unit of time. In some aspects, OCR unit 630 is used to extract a measurement unit from the waveform portion of the image and DSP unit 634 uses the period and the measurement unit to extract operational and/or medical data. For example, OCR unit 630 determines that the waveform portion of the image displays placement signal and/or motor current over a period of ten seconds, and DSP unit 634 associates each pixel in the waveform portion with a corresponding placement signal and/or motor current, and a unit of time equal to the period divided by the number of pixels in the waveform portion of the image.

Operational and/or medical data unit 632 may be an application that databases and organizes the data extracted from OCR unit 630 and/or DSP unit 634. For example, operational data unit 632 identifies the type of data extracted by OCR unit 630 and/or DSP unit 634, and categorize the data into operational and/or medical conditions. Operational and/or medical conditions may include pressure, flow rate, pump speed, temperature, voltage, current, and biometric conditions.

Remote link architecture 600 can be implemented with process 200, process 300, and process 500 to control the bandwidth, quality, and type of video streaming from remote link devices 102. Remote link architecture 600 may be scaled to an indefinite amount of remote link devices 102 and client devices 104. OCR unit 630 and operational data unit 632 may be included in another component of remote link architecture 100, remote link architecture 400, remote link architecture 600, or remote link architecture 700 (described below).

Figure 7:
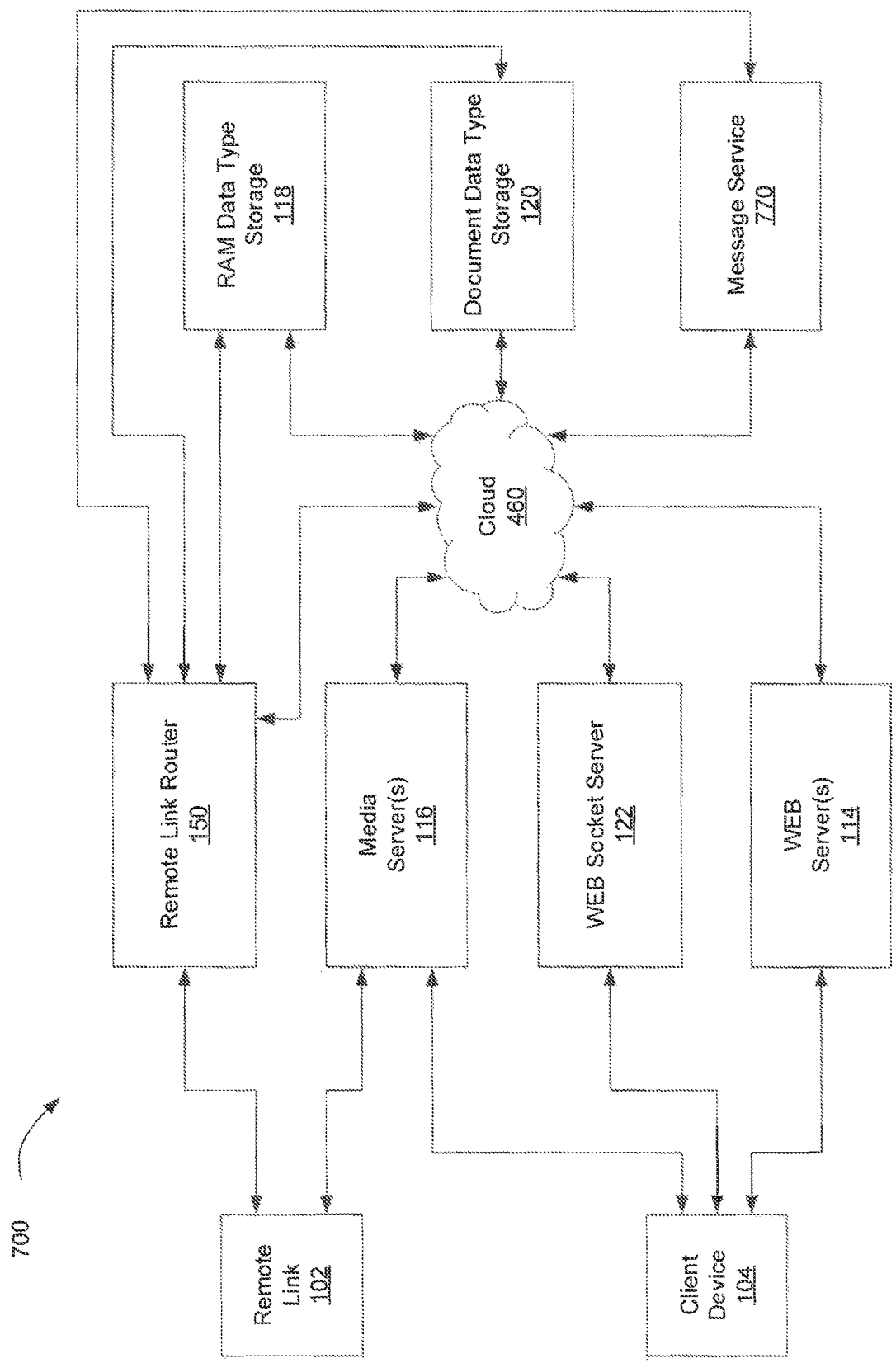
FIG. 7 shows a schematic representation of a remote link architecture, configured according to one or more aspects of the present disclosure.

FIG. 7 is a schematic representation of a remote link architecture 700. Remote link architecture 700 includes remote link 102, client device 104, RLR 150, media server 116, WEB socket server 122, WEB server 114, cloud 460, RAM data type storage 118, document data type storage 120, and message service 770.

Remote link 102 may be embedded in a medical device that is monitoring a patient at a hospital, clinic, the patient's house, or another location. Remote link 102 may capture images and deliver video streams from the medical device display and transmit the images and video to the remote link router 150. Remote link architecture 100 may comprise multiple remote links 102. Remote link 102 interacts with the rest of remote link architecture 100 through RLR 150.

Client device 104 may be a personal computer, a tablet, or a mobile device with an internet connection. A medical professional using client device 104 may be interested in obtaining information from one or multiple remote links 102. Images captured by a remote link 102 may be accessed by the client device 104. In addition, if the medical professional is interested in observing a live video stream of the medical device embedded with remote link 102, the client device can display the video stream. Remote link architecture may comprise multiple client devices 104. A single client device 104 may access multiple remote links 102, as long as the client device has access to the remote links 102.

WEB server 114 may include a mechanism for clients to view information, data, and video streams from one or more remote links 102. WEB socket server 122 may push messages to groups of client devices 104. Upon client device 104 connection to the WEB server 114, the client device 104 will register to the WEB socket server 122 for messages for either one or multiple remote links 102. The WEB socket server 122 will receive messages that will be applicable to one or more remote links 102. This message with associated data will be broadcasted to all connected client devices 104 for updates from those remote links 102. Message service 770 may manage the transfer of messages between the different components of remote link architecture 700 through cloud 460. Cloud 460 represents a network of internet-based devices and connections such as servers, storage, and applications.

Media server 116 may be the receiver and sender of video streams from one or more remote links 102. Media server 116 may be similar to video server 116 described above. Media server 116 may also be the receiver and sender of images captured from one or more remote links 102.

RAM data type storage 118 may be volatile storage that can be accessed quickly. RAM data type storage 118 may comprise dynamic random-access memory (DRAM), static random-access memory (SRAM), or another type of high-speed volatile memory. Images captured by remote link 102 may be stored in RAM data type storage 118 before being transmitted to client device 104. RAM data type storage 118 may also store video streams captured by remote link 102. Document data type storage 120 may be non-volatile storage that can maintain data for long periods of time. Document data type storage 120 may be hard disks, optical disks, solid-state drives (SSDs), or another type of non-volatile memory.

Figure 8:
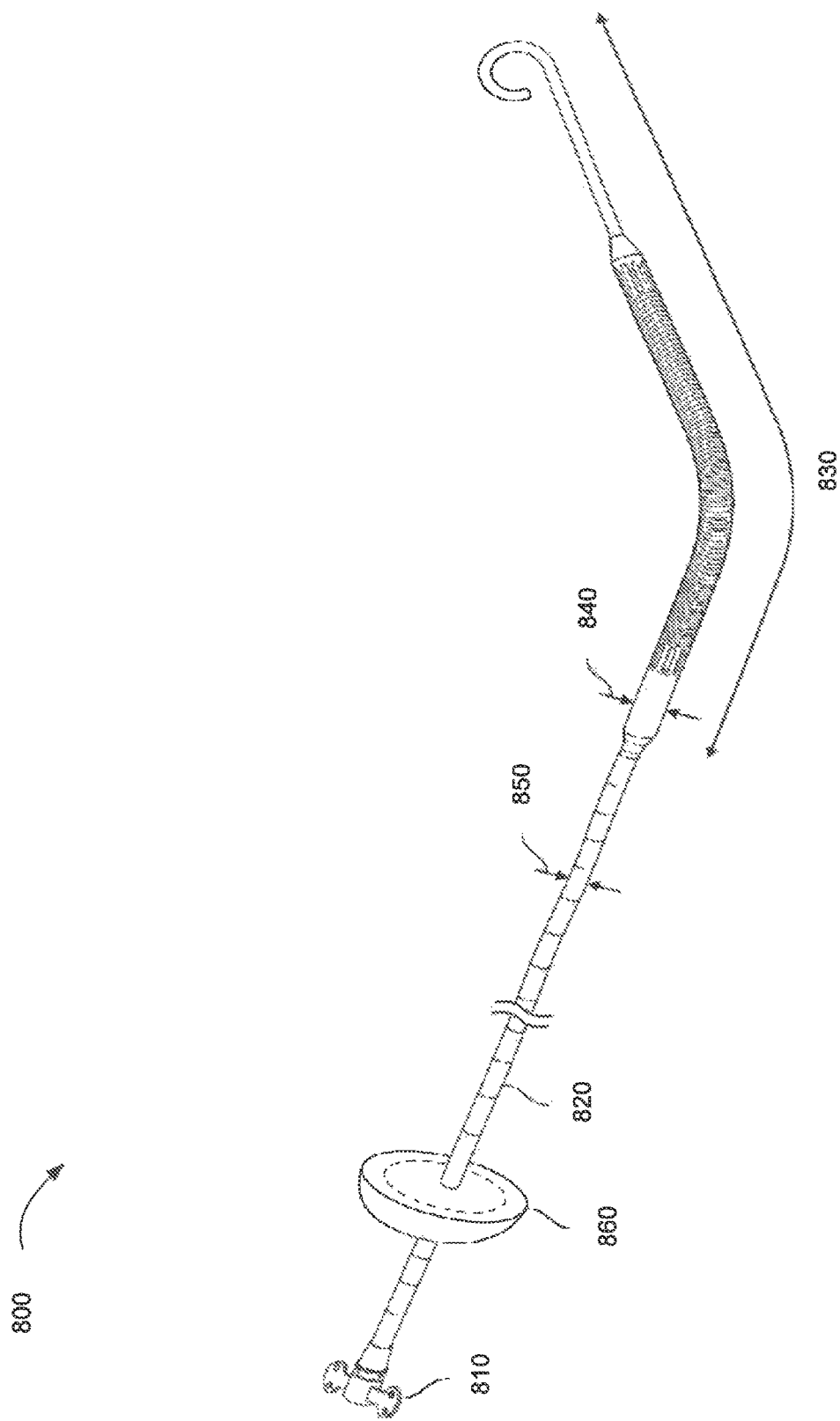
FIG. 8 shows a schematic representation of a medical device, configured according to one or more aspects of the present disclosure.

FIG. 8 shows an illustrative medical device such as an intravascular blood pump 800 according to certain implementations. The pump 800 comprises a pump handle 810, a pump head 830, a catheter 820 connecting the pump handle 810 to the pump head 830, and a connecting hub 860. The catheter 820 is tubular and has a substantially uniform outer diameter 850. The catheter 820 enables the pump head 830 and the pump handle 810 to be in electro-mechanical communication. The pump handle 810 is in communication with control circuitry which allows the control of the pump head 830. The pump head 830 contains electro-mechanical components that enable the device to perform various tasks within the body of a patient, such as pump blood from a location within the body. The pump head 830 has a diameter 840 that is larger than the diameter 850 of the catheter 820. An example of such a percutaneous pump is the Impella 2.5® system (Abiomed, Inc., Danvers, Mass.) which includes the pump and an Automatic Impella Controller (AIC).

Figure 9:
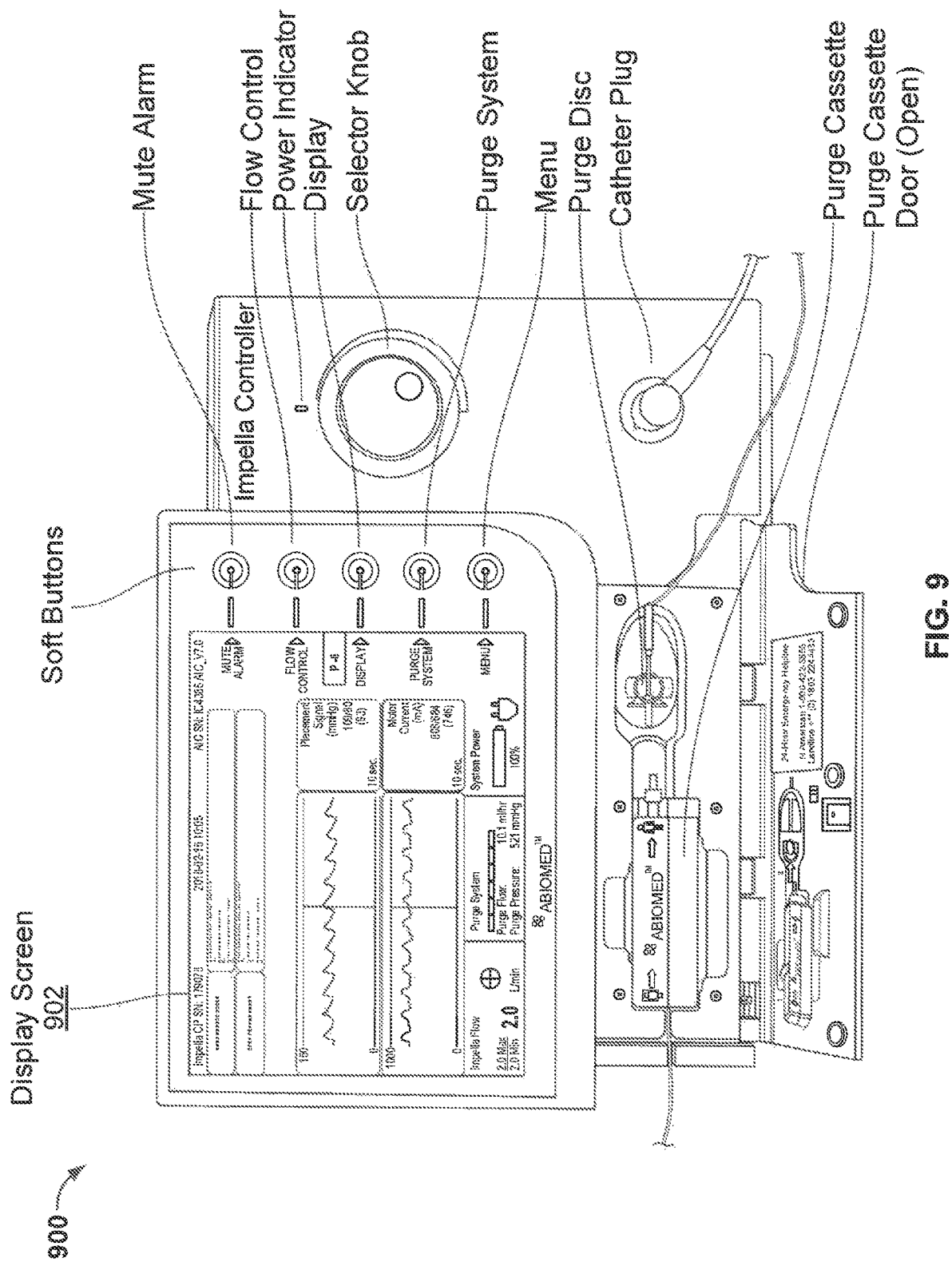
FIG. 9 shows an exemplary medical device controller, configured according to one or more aspects of the present disclosure.

FIG. 9 shows an exemplary medical device controller 900, such as the AIC, configured according to one or more aspects of the present disclosure. The medical device controller 900 provides an interface for monitoring and controlling the functions of pump 800. Medical device controller 900 may include display screen 902 that may display images from a video stream where the images illustrate data associated with a medical device such as an intravascular blood pump 800 over a period of time. In certain implementations, display screen 902 displays real-time operating and/or medical data associated with the pump 800.

Figure 10:
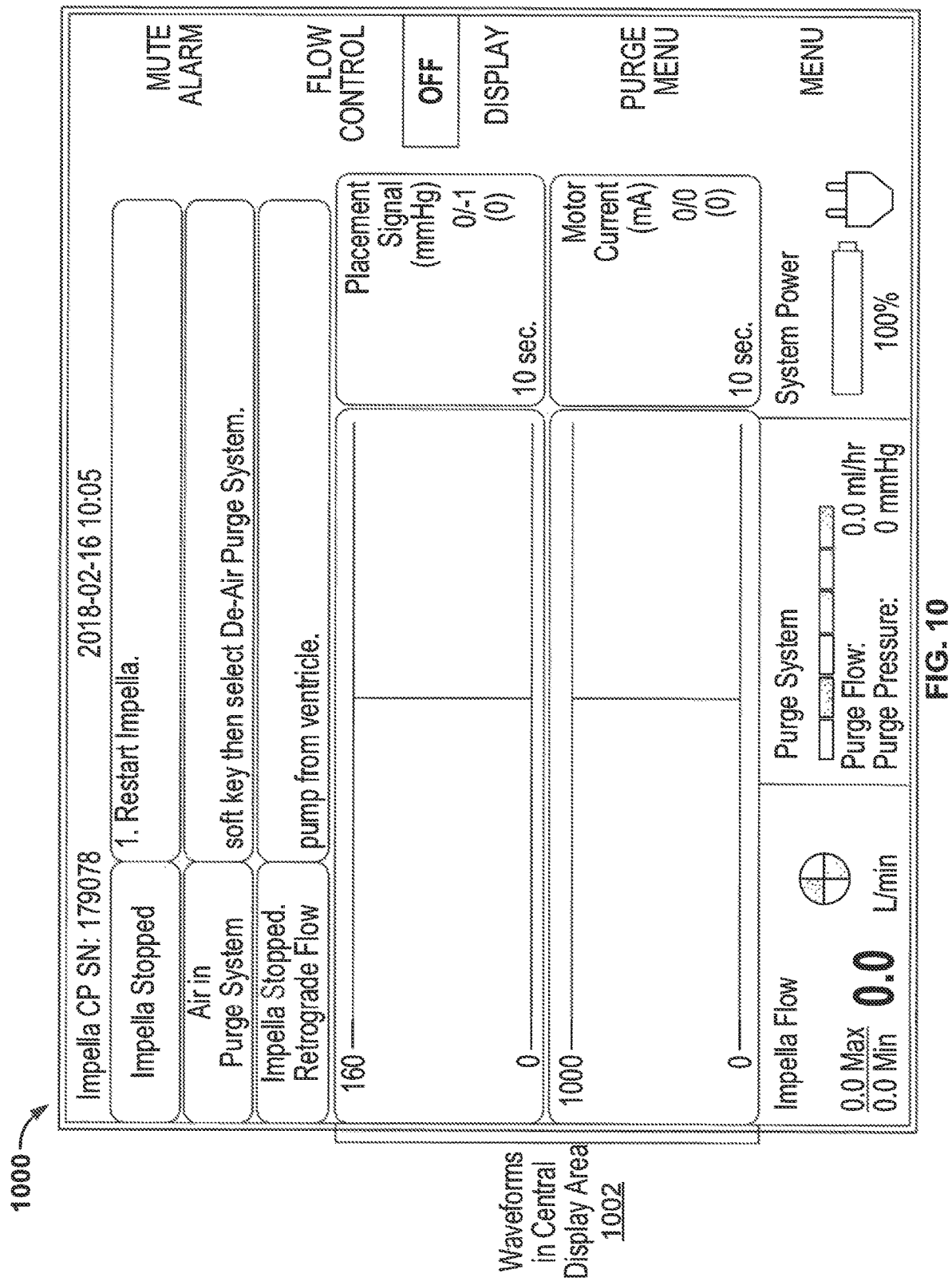
FIG. 10 shows an exemplary image displayed on a medical device controller screen, configured according to one or more aspects of the present disclosure.

FIG. 10 shows an exemplary image 1000 displayed on, for example, the display screen 902, configured according to one or more aspects of the present disclosure. In some configurations, the image 1000 may be captured by an intermediate device or data module such as remote link 102 via a network and transmitted to another device such as, for example, media server 116. Image 1000 may include waveforms 1002. Waveforms 1002 illustrate medical and/or operational data corresponding to the operation of pump 800. Examples of medical data illustrated by waveforms 1002 include placement signal and motor current. The waveforms 1002, such as the motor current waveform may provide a history, representation, and/or illustration of motor current over a period time (e.g., 10 seconds). In this way, the image 1000 includes motor current data (and other data) associated with pump 800 over a 10 second period of time. Hence, in one implementation, a data module 102 continuously monitors a video stream output from the device controller 900, but only periodically capture an image such as image 1000. Then the data module 102 transmits the image 1000 to another device, such as server 116, which converts the illustrated waveforms 1002 to medical and/or operation data using, for example, OCR. If, for example, the waveforms 1002 illustrate medical data over a 10 second period, the data module 102 may capture successive images 1000 every 10 second (at 10 second intervals) to ensure that there are no gaps in the data provided to server 116. Processes 1300 and 1400, as discussed in relation to FIGS. 13 and 14 below, describe exemplary methods of extracting data from an image and determining the validity of the extracted data, respectively.

Figure 11:
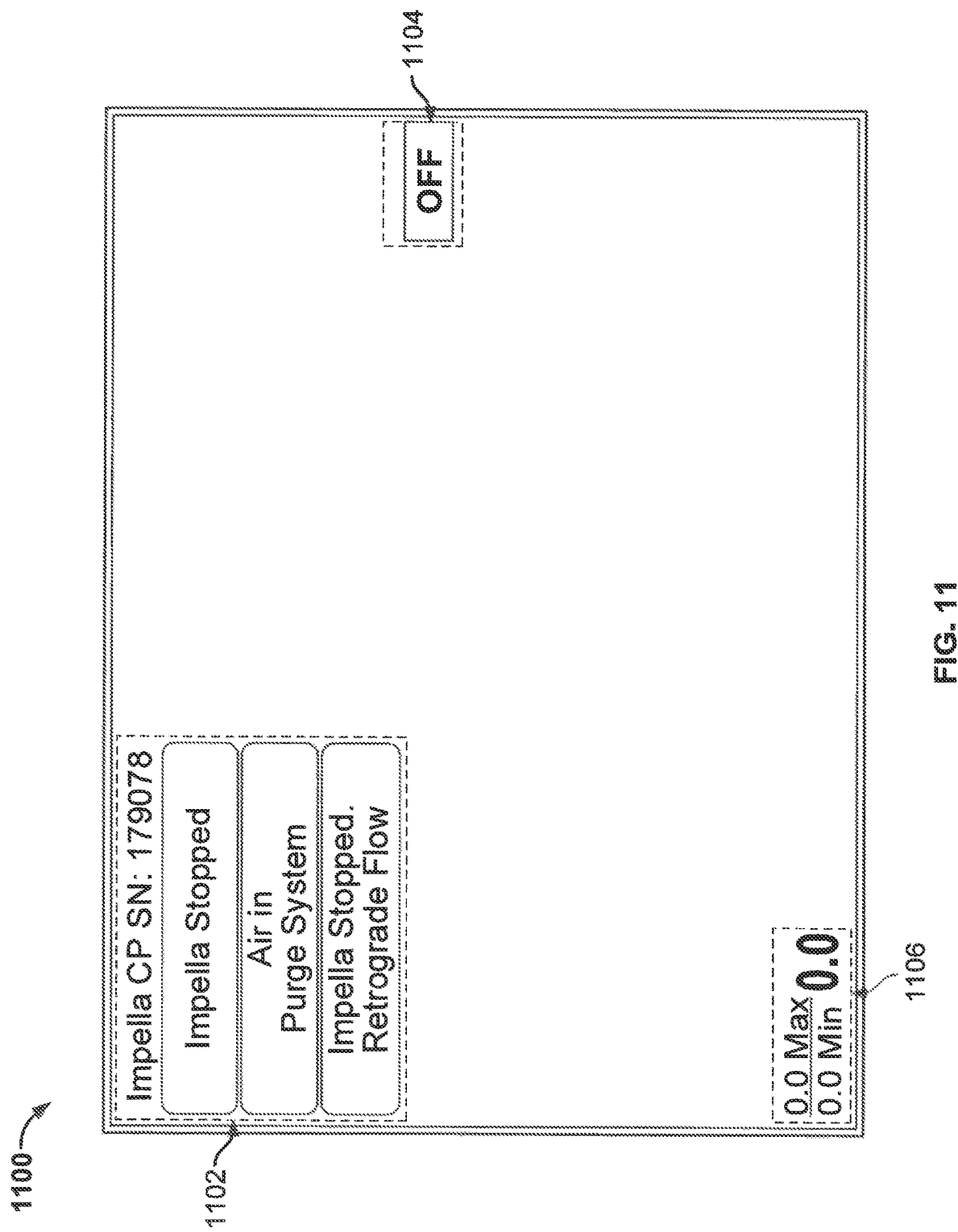
FIG. 11 shows the exemplary image of FIG. 10 after removing select portions of the image, configured according to one or more aspects of the present disclosure.

In one aspect, server 116 masks certain portions of image 1000 before extracting the data using OCR unit 630 or an equivalent. FIG. 11 shows an exemplary image 1100, configured according to one or more aspects of the present disclosure. Image 1100 is a masked version of image 1000 that has been stripped of certain portions of image 1000. For example, all portions of image 1000 are stripped except alarm and serial number portion 1102, performance level portion 1104, and flow level portion 1106. After generating image 1100, server 116 performs image processing to clarify and enlarge alarm and serial number portion 1102, performance level portion 1104, and flow rate portion 1106.

Figure 12:
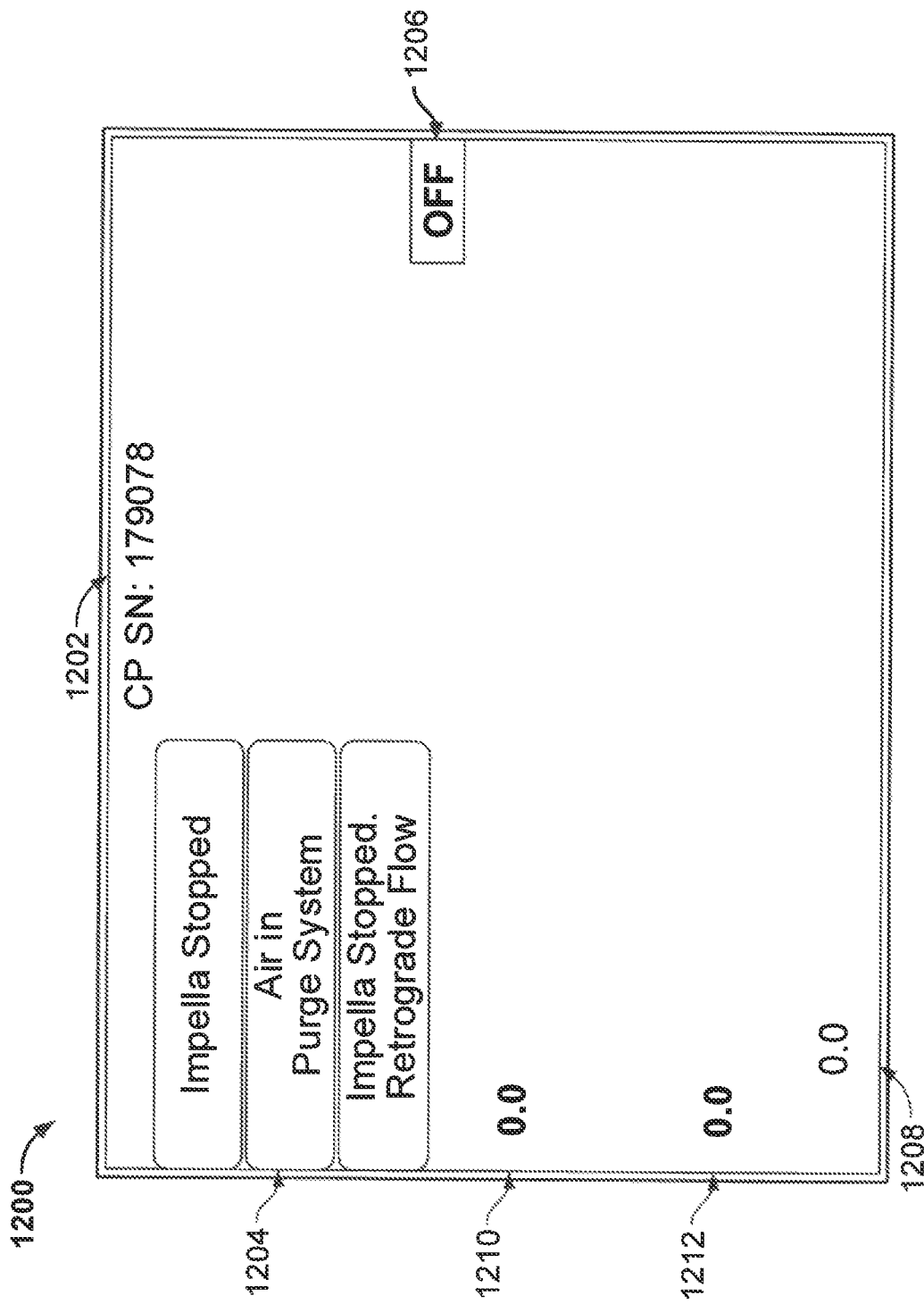
FIG. 12 shows an exemplary image of the remaining portions of the image of FIG. 11, configured according to one or more aspects of the present disclosure.

FIG. 12 shows an exemplary image 1200, configured according to one or more aspects of the present disclosure. Image 1200 is a processed version of image 1100 in order to facilitate the extracting of data using OCR unit 630. In one aspect, alarm and serial number portion 1102 may be processed into serial number portion 1202 and alarm portion 1204. Serial number portion 1202 includes a certain number of digits that identify the medical device 624 that is currently being monitored and may be enlarged to facilitate OCR. For example, serial number portion 1202 includes six digits. Alarm portion 1204 may indicate the type of alarm that the medical device 624 may be experiencing. For example, alarm portion 1204 includes pixels of a color that indicate a severity of the alarm the medical device 624 may be experiencing. Examples of the colors in the alarm portion 1204 include red, yellow, and green. In some aspects, performance level portion 1206 indicates the performance level of the pump 800 and includes three characters. Examples of the characters in the performance level portion 1206 may include "OFF", "P-0", "P-1", "P-2", "P-3", "P-4", "P-5", "P-6", "P-7", "P-8", and "P-9". Performance level portion 1206 may be an enlarged version of performance level portion 1104. In another aspect, flow rate portion 1106 may be processed into present flow rate portion 1208, max flow rate portion 1210, and min flow rate portion 1212. Present flow rate portion 1208 indicates the present flow rate of pump 800 in units of liters per minute. Correspondingly, max flow rate portion 1210 and min flow rate portion 1212 indicate the range of the flow rate of the pump 800, respectively, and may be enlarged to facilitate OCR. Present flow rate portion 1208, max flow rate portion 1210, and min flow rate portion 1212 includes three characters that range from "0.0" to "9.9".

Figure 13:
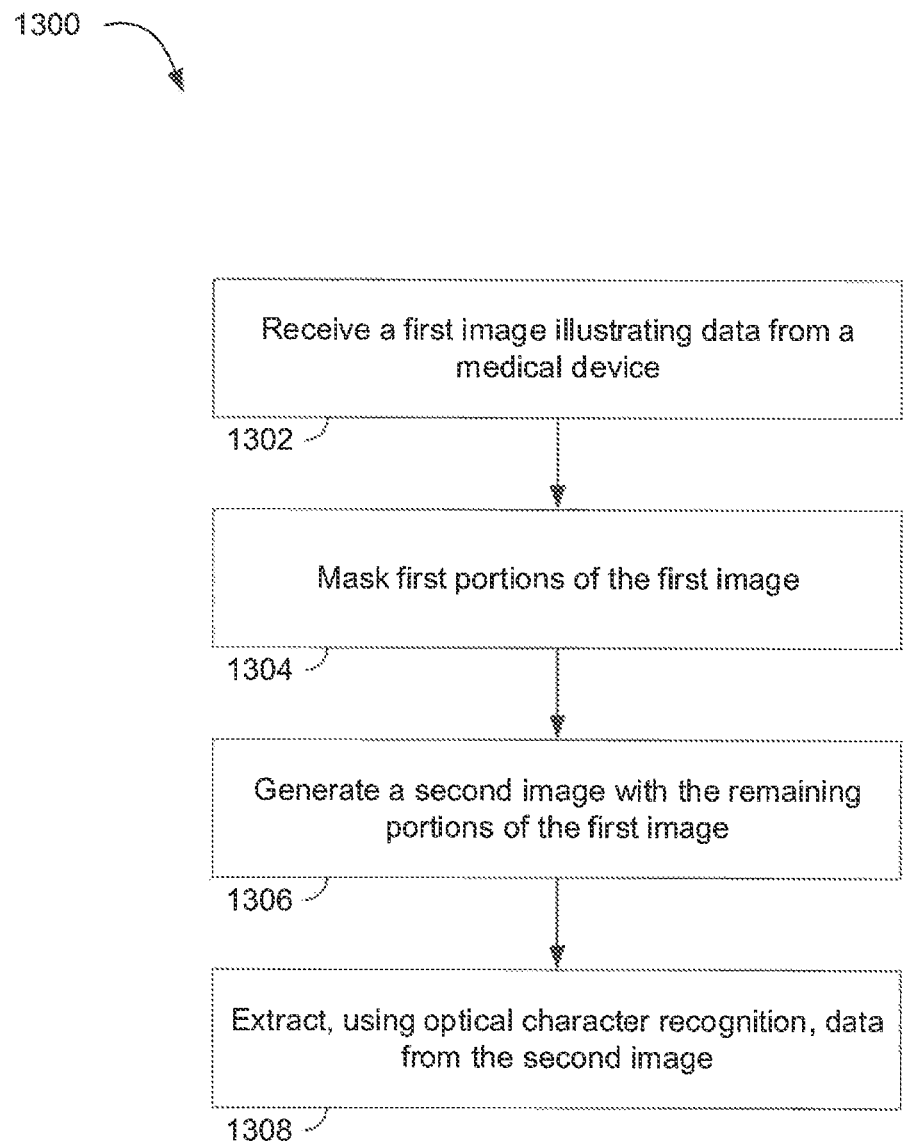
FIGS. 13 and 14 are flow diagrams of method steps for extracting data from an image and determining the validity of the extracted data, according to an aspect of the present disclosure.

A process 1300 of extracting data from an image is illustrated in FIG. 13. Process 1300 begins by receiving a first image illustrating data from a medical device 624 at step 1302. For example, remote link 102 captures image 1000 using image capture unit 628 and server 116 receives image 1000 from remote link 102.

Process 1300 continues by masking first portions of the first image at step 1304. For example, server 116 uses an image mask to occlude portions of image 1000 that will not be sent to OCR unit 630 for data extraction. Masking select portions of an image allows for improved efficiency of image processing because only the select portions of the image that are not masked will be sent to OCR unit 630 or DSP unit 634. By masking select portions of the image, less data is transmitted between server 116, OCR unit 630, and DSP unit 634, and OCR unit 630 and DSP unit 634 require less processing to extract data from the image. In one aspect, server 116 may generate image 1100 by using the image mask to strip image 1000 of certain portions of image 1000. For example, server 116 generates image 1100 by using the image mask to strip image 1000 of all portions except alarm and serial number portion 1102, performance level portion 1104, and flow level portion 1106. In another aspect, server 116 may select a different mask corresponding to features of image 1000. For example, server 116 selects a different mask based on the size of image 1000 or the GUI version corresponding to image 1000. For example, server 116 selects a mask based on a software version of the remote link 102. In some aspects, server 116 may select a mask based on the type of display screen 902 being used. For example, if the image displayed on display screen 902 is not the appropriate image for the first mask selected by server 116, server 116 determines that the first mask used is not the appropriate mask for image 1000 and select a different mask based on the image currently being displayed on display screen 902. In one aspect, server 116 may wait to mask portions of image 1000 until the appropriate image is being displayed on display screen 902. In another aspect, server 116 may select a mask based on the amount of data to be extracted from image 1000.

Process 1300 continues by generating a second image with the remaining portions of the first image at step 1306. For example, server 116 generates image 1200 by performing image processing to clarify and enlarge alarm and serial number portion 1102, performance level portion 1104, and flow rate portion 1106. In one aspect, server 116 may generate serial number portion 1202 and alarm portion 1204 from serial number portion 1102, performance level portion 1206 from performance level portion 1104, and present flow rate portion 1208, max flow rate portion 1210, and min flow rate portion 1212 from flow rate portion 1106.

Process 1300 finishes by extracting, using optical character recognition, data from the second image at step 1308. For example, the serial number of medical device 624, the type of alarm currently being indicated, the performance level of the pump 800, and the flow rate are extracted from image 1200 using OCR unit 630. In one aspect, OCR unit 630 may select a pixel from the second image to determine an alarm severity from alarm portion 1204. For example, OCR unit 630 determines the color of the pixel and determine the alarm severity based on the color of the pixel. In some aspects, OCR unit 630 may select two different pixels from the second image to determine the alarm severity from alarm portion 1204. For example, storage 120 stores a database of alarm types and alarm severity levels and corresponding alarm color. Server 116 may access the database stored in storage 120 and determine the alarm type and severity level associated with the color of the pixel or pixels from alarm portion 1204. In another aspect, OCR unit 630 may select a first pixel at a first time and a second pixel at a second time. For example, in some instances where image 1000 is defective when received by server 116, server 116 is not able to determine the color of a pixel from the second image at the first time. Server 116 receives another image 1000 to determine the color of another pixel from the second image at the second time. In other aspects, server 116 determines the alarm severity to be the same as the previous alarm severity if server 116 cannot determine the color of the pixel from the two pixels. In another aspect, process 1400, described below, may be used to validate the extracted data from the second image.

Figure 14:
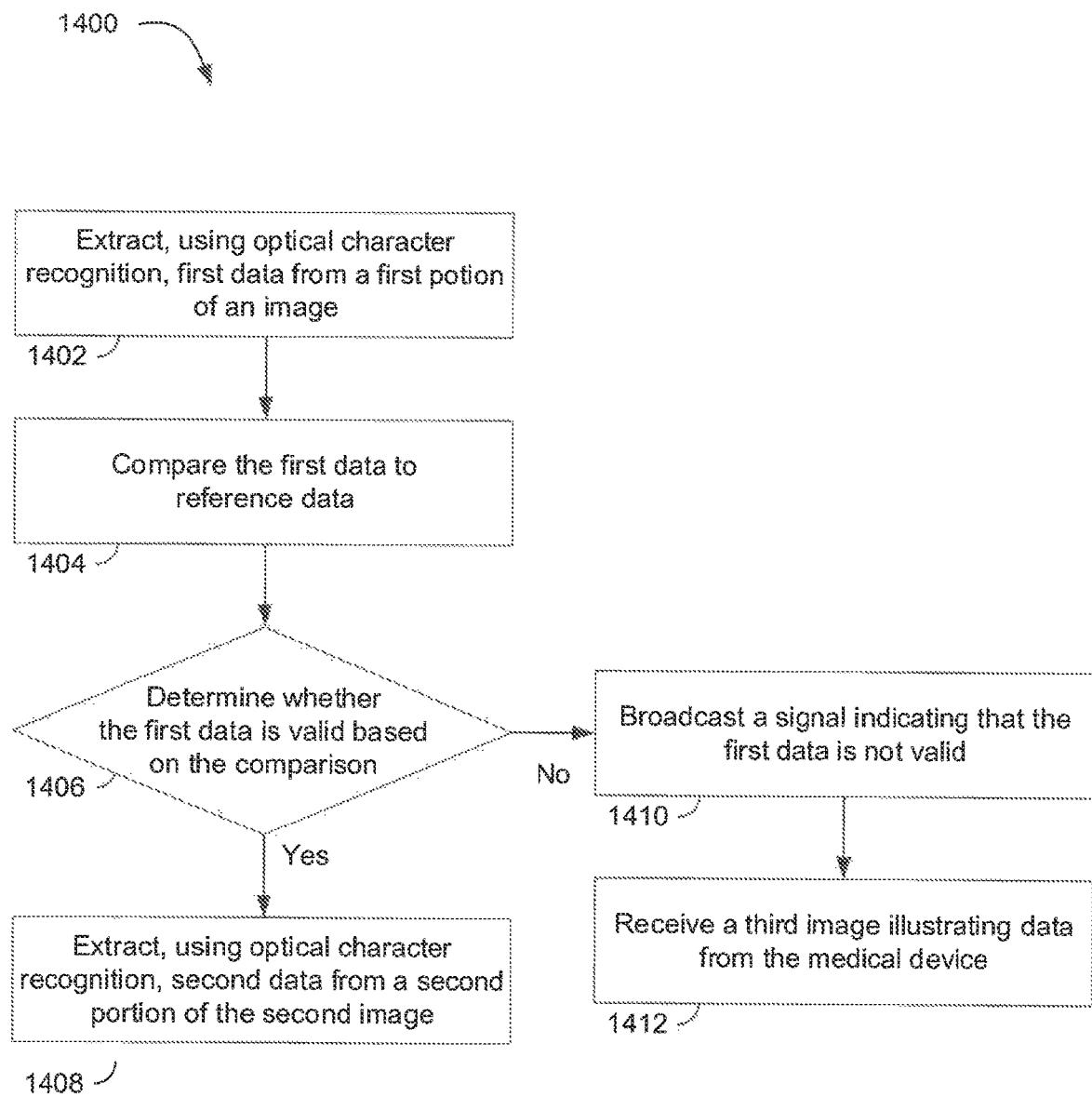

A process 1400 of determining the validity of data from an image is illustrated in FIG. 14. Process 1400 begins by extracting, using optical character recognition, first data from a first portion of an image at step 1402. For example, the serial number of medical device 624 is extracted from serial number portion 1202. In one aspect, process 1300, described above, may be used to perform extraction of first data from the first portion of the image.

Process 1400 continues by comparing the first data to reference data at step 1404. In one aspect, reference data may include a certain number of characters and/or digits that represent standard formats that may represent the first data. For example, the extracted serial number of medical device 624 is compared with possible serial numbers stored in document data type storage 120. Additional examples of comparing data to reference data are described in U.S. Pat. No. 9,002,083, entitled "System, Method, and Software for Optical Device Recognition Association," the entire contents of which are hereby incorporated by reference.

Process 1400 continues by determining the validity of the first data based on the comparison at step 1406. For example, if the extracted serial number of medical device 624 does not match a standard format for a serial number consisting e.g. of a certain number of characters and/or digits, the extracted serial number is not valid. In one aspect, if the extracted serial number does not comprise six digits and the standard format for the serial number is six digits, the extracted serial number is not valid. In another aspect, step 1406 repeats a certain amount of times before making a final determination. For example, if three attempts are required to validate the first data, the first data is determined to be valid if comparison results in a positive match three times. If during the three attempts one of the comparisons does not result in a positive match, the first data is determined to not be valid.

In response to determining that the first data is valid based on the comparison, process 1400 continues to step 1408. At step 1408, process 1400 continues by extracting, using optical character recognition, second data from a second portion of the second image. For example, the performance level of pump 800 is extracted from performance level portion 1206. As described in relation to FIG. 12, examples of the characters in the performance level portion 1206 may include "OFF", "P-0", "P-1", "P-2", "P-3", "P-4", "P-5", "P-6", "P-7", "P-8", and "P-9". In one aspect, process 1400 may continue to step 1402 until all data from the portions of image 1200 have been extracted.

In response to determining that the first data is not valid based on the comparison. Process 1400 continues to step 1410. At step 1410, process 1400 continues by broadcasting a signal indicating that the first data is not valid. For example, server 116 notifies the remote link 102 that image 1000 produced invalid first data.

Process 1400 finishes by receiving a third image illustrating data from the medical device at step 1412. For example, remote link 102 captures another image similar to 1000 using image capture unit 628 and server 116 may receive the similar image from remote link 102. In one aspect, process 1400 may continue to step 1402 until all data from the portions of image 1200 have been extracted.

It will be understood that while a percutaneous heart pump is described herein, any other medical device can be used on conjunction with the present disclosure. Furthermore, while FIGS. 8 and 9 show a media device configuration where a controller 900 is separate from a pump 800, one of ordinary skill readily recognizes that a medical device may be configured such that the controller and pump (or other elements) are integrated in the same housing.

Other objects, advantages and aspects of the various aspects of the present invention will be apparent to those who are skilled in the field of the invention and are within the scope of the description and the accompanying Figures. For example, but without limitation, structural or functional elements might be rearranged consistent with the present invention. Similarly, principles according to the present invention could be applied to other examples, which, even if not specifically described here in detail, would nevertheless be within the scope of the present invention.

I claim:

1. A method comprising:
   generating, with a medical device controller, a video stream of data associated with an intravascular blood pump communicatively coupled to the medical device controller;
   receiving, with a remote link, the video stream generated by the medical device controller;
   capturing, with the remote link, at least one image from the video stream, wherein the first at least one image illustrates a motor current waveform;
   receiving, with a server, the at least one image captured by the remote link; and
   extracting, with an optical character recognition (OCR) unit and a digital signal processing (DSP) unit of the server, motor current data from the motor current waveform, wherein the OCR unit is configured to extract a first period of time of the first motor current waveform from a first portion of the first at least one image, and
   wherein the DSP unit is configured to use the first period of time and boundaries of the first portion to associate one or more pixels in the first portion with a first unit of time.

2. The method of claim 1, wherein the at least one image comprises additional data relating to at least one of pressure, flow rate, pump speed, temperature, voltage, current, or biometric conditions.

3. The method of claim 2 further comprising:
   measuring the additional data via at least of one of a pressure sensor, temperature sensor, flow rate sensor, voltage sensor, current sensor, optical sensor, or audio sensor.

4. The method of claim 1, wherein the at least one image further illustrates a placement signal waveform, and wherein the method further comprises:
   extracting, with the OCR unit and the DSP unit of the server, placement data from the placement signal waveform,
   wherein the OCR unit is configured to extract a second period of time of the placement signal waveform from a second portion of the at least one image, and
   wherein the DSP unit is configured to use the second period of time and boundaries of the second portion to associate one or more pixels in the second portion with a second unit of time.

5. The method of claim 4, wherein extracting the motor current data from the motor current waveform comprises masking one or more portions of the at least one image, and wherein the one or more masked portions do not include the first portion and the second portion of the at least one image.

6. The method of claim 1 further comprising:
   transmitting, with the remote link, a first signal to a router that indicates that the remote link is connected to a data network;
   transmitting, with the router, a command to the remote link to start capturing the first at least one image;
   transmitting, with the remote link, the at least one image to the router;
   broadcasting, with the router, a second signal indicating that the remote link has captured the at least one image;
   receiving, with the server, the broadcasted second signal from the router; and
   storing, with the server, the at least one image in a database.

7. The method of claim 1, wherein the at least one image further comprises pressure data from a pressure sensor of the intravascular blood pump, and wherein the method further comprises extracting, with the server, the pressure data from the at least one image.

8. The method of claim 7, wherein the at least one image further comprises alarm data associated with the intravascular blood pump, and wherein the method further comprises extracting, with the server, the alarm data from the at least one image.

9. The method of claim 1, wherein the at least one image further comprises a serial number of the intravascular blood pump, and wherein the method further comprises:
   extracting, with the OCR unit of the server, the serial number from the at least one image; and
   determining, with the server, a validity of the motor current data based on a comparison between the serial number and one or more predetermined values stored in a database.

10. The method of claim 1, wherein extracting the motor current data from the motor current waveform comprises masking one or more portions of the at least one image.

11. The method of claim 10, wherein the one or more masked portions do not include the first portion of the at least one image.

12. A system comprising:
   an intravascular blood pump comprising a motor;
   a medical device controller configured to:
      monitor the intravascular blood pump; and
      generate a video stream;
   a remote link configured to:
      receive the video stream generated by the medical device controller; and
      capture at least one image from the video stream, wherein the at least one image illustrates a motor current waveform; and
   a server comprising an optical character recognition (OCR) unit and a digital signal processing (DSP) unit, wherein the server is configured to:
      receive the at least one image captured by the remote link; and
      extract, with the OCR unit and the DSP unit, motor current data from the motor current waveform,
      wherein the OCR unit is configured to extract a first period of time of the motor current waveform from a first portion of the at least one image, and
      wherein the DSP unit is configured to use the first period of time and boundaries of the first portion to associate one or more pixels in the first portion with a first unit of time.

13. The system of claim 12, wherein the at least one image comprises additional data relating to at least one of pressure, flow rate, pump speed, temperature, voltage, current, or biometric conditions.

14. The system of claim 13, wherein the additional data is measured via at least of one of a pressure sensor, temperature sensor, flow rate sensor, voltage sensor, current sensor, optical sensor, or audio sensor.

15. The system of claim 12, wherein the at least one image further illustrates a placement signal waveform, wherein the server is further configured to extract, with the OCR unit and the DSP unit, placement data from the placement signal waveform, wherein the OCR unit is further configured to extract a second period of time of the motor current waveform from a second portion of the at least one image, and wherein the DSP unit is further configured to use the second period of time and boundaries of the second portion to associate one or more pixels in the second portion with a second unit of time.

16. The system of claim 15, wherein extracting the motor current data from the motor current waveform comprises masking one or more portions of the at least one image, and wherein the one or more masked portions do not include the first portion and the second portion of the at least one image.

17. The system of claim 12, wherein the remote link is further configured to:
   transmit a first signal to a router that indicates that the remote link is connected to a data network;
   receive a command from the router to start capturing the at least one image; and
   transmit the at least one image to the router,
   wherein the router is configured to broadcast a second signal indicating that the remote link has captured the at least one image, and
   wherein the server is configured to receive the broadcasted second signal from the router and store the first at least one image in a database.

18. The system of claim 12, wherein the intravascular blood pump further comprises a pressure sensor, wherein the at least one image further comprises pressure data from the pressure sensor of the intravascular blood pump, and wherein the server is further configured to extract the pressure data from the at least one image.

19. The system of claim 18, wherein the at least one image further comprises alarm data associated with the intravascular blood pump, and wherein the server is further configured to extract the alarm data from the at least one image.

20. The system of claim 12, wherein the at least one image further comprises a serial number of the intravascular blood pump, and wherein the server is further configured to:
   extract the serial number from the at least one image with the (OCR) unit; and
   determine a validity of the motor current data based on a comparison between the serial number and one or more predetermined values stored in a database.

21. The system of claim 12, wherein extracting the motor current data from the motor current waveform comprises masking one or more portions of the at least one image.

22. The system of claim 21, wherein the one or more masked portions do not include the first portion of the at least one image.

23. The system of claim 12, wherein the remote link is embedded in the medical device controller.

* * * * *

UNITED STATES PATENT AND TRADEMARK OFFICE
CERTIFICATE OF CORRECTION

PATENT NO. : 11,217,344 B2
APPLICATION NO. : 15/941695
DATED : January 4, 2022
INVENTOR(S) : Alessandro Simone Agnello It is certified that error appears in the above-identified patent and that said Letters Patent is hereby corrected as shown below:

In the Specification

Column 5, Line 35:
Now reads: "626"; should read -- 628 --

In the Claims

Column 14, Claim 1, Line 4:
Now reads: "wherein the first"; should read -- wherein the --

Column 14, Claim 1, Line 11:
After "waveform,": insert a line break, the new line beginning with the word "wherein"

Column 14, Claim 1, Line 12:
Now reads: "of the first motor"; should read -- of the motor --

Column 14, Claim 1, Line 13:
Now reads: "portion of the first"; should read -- portion of the --

Column 14, Claim 3, Line 25:
Now reads: "at least of one"; should read -- at least one --

Column 14, Claim 6, Line 52:
Now reads: "capturing the first"; should read -- capturing the at --

Column 15, Claim 14, Line 49:
Now reads: "at least of one"; should read -- at least one --

Column 16, Claim 17, Line 26:
Now reads: "store the first"; should read -- store the at least --

Signed and Sealed this
Fifth Day of July, 2022

Katherine Kelly Vidal
*Director of the United States Patent and Trademark Office*

Column 16, Claim 20, Line 42:
Now reads: "(OCR)"; should read -- OCR --